United States Patent
Coelho et al.

[11] Patent Number: 6,123,696
[45] Date of Patent: Sep. 26, 2000

[54] CENTRIFUGATION BAG WITH YIELDABLE PARTITIONS

[75] Inventors: Philip Henry Coelho, El Dorado Hills, Calif.; Pablo Rubinstein, New York, N.Y.

[73] Assignee: ThermoGenesis Corp., Rancho Cordova, Calif.

[21] Appl. No.: 09/118,688

[22] Filed: Jul. 16, 1998

[51] Int. Cl.[7] .................................... B04B 7/18
[52] U.S. Cl. .......................... 604/410; 494/45; 210/787; 604/416; 206/219
[58] Field of Search .................................. 210/780, 781, 210/782, 787, 789, 512.1, 446; 604/408, 409, 410, 406, 416; 422/102; 494/45; 206/219, 221, 222; 383/38, 41

[56] References Cited

U.S. PATENT DOCUMENTS

| | | |
|---|---|---|
| 3,257,072 | 6/1966 | Reynolds . |
| 3,945,928 | 3/1976 | Ayres . |
| 3,987,961 | 10/1976 | Sinn et al. . |
| 4,617,009 | 10/1986 | Ohlin et al. . |

OTHER PUBLICATIONS

NPBI International BV, Compomat® G4 and Compomaster® Two Brochure, entire brochure (no date).

*Primary Examiner*—W. L. Walker
*Assistant Examiner*—A. L. Schwartz
*Attorney, Agent, or Firm*—Bernhard Kreten

[57] ABSTRACT

A method and apparatus for the sequestration of components of a fluid by forcing heavier fractions of the fluid to pass beyond a yieldable partition integrally formed within a bag. Fluid fractions remain sequestered within bag compartments when forces driving the heavier fraction have been removed.

18 Claims, 2 Drawing Sheets

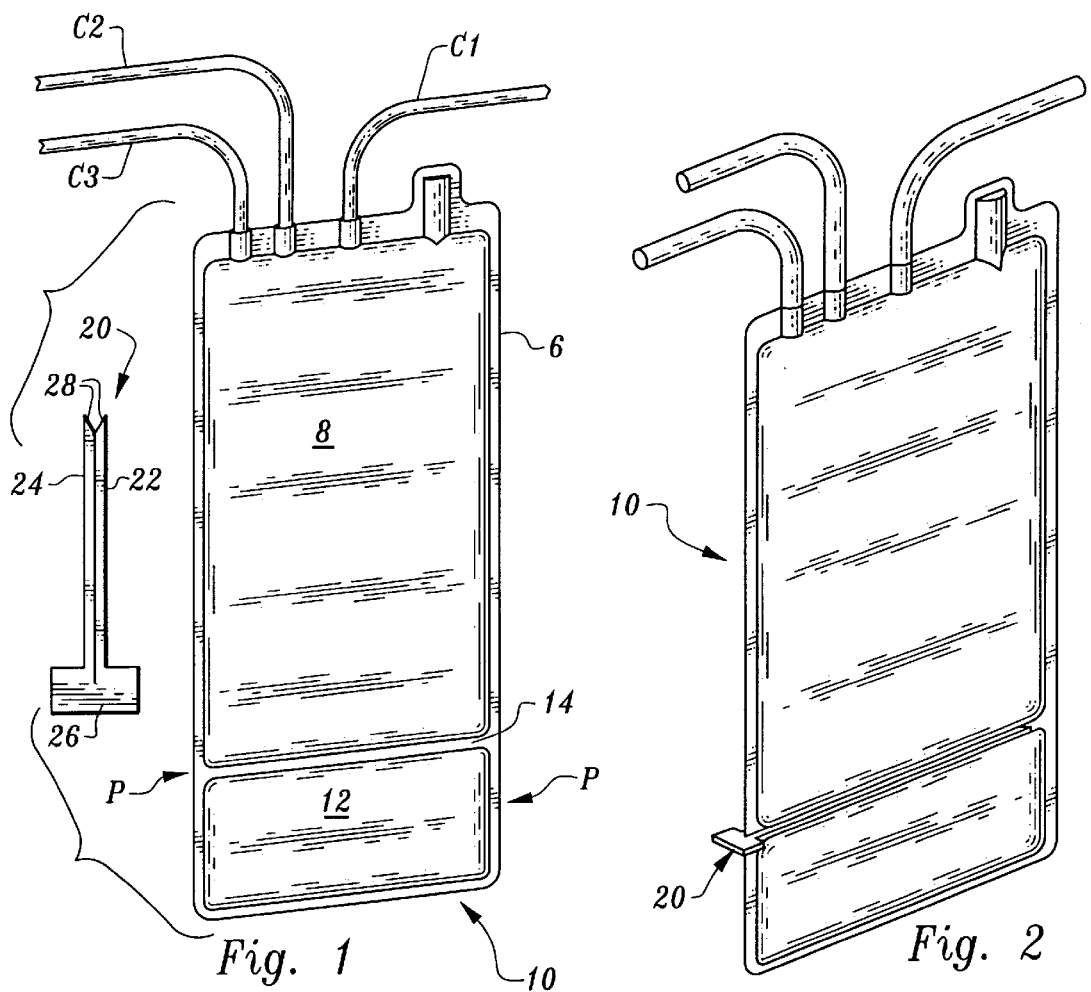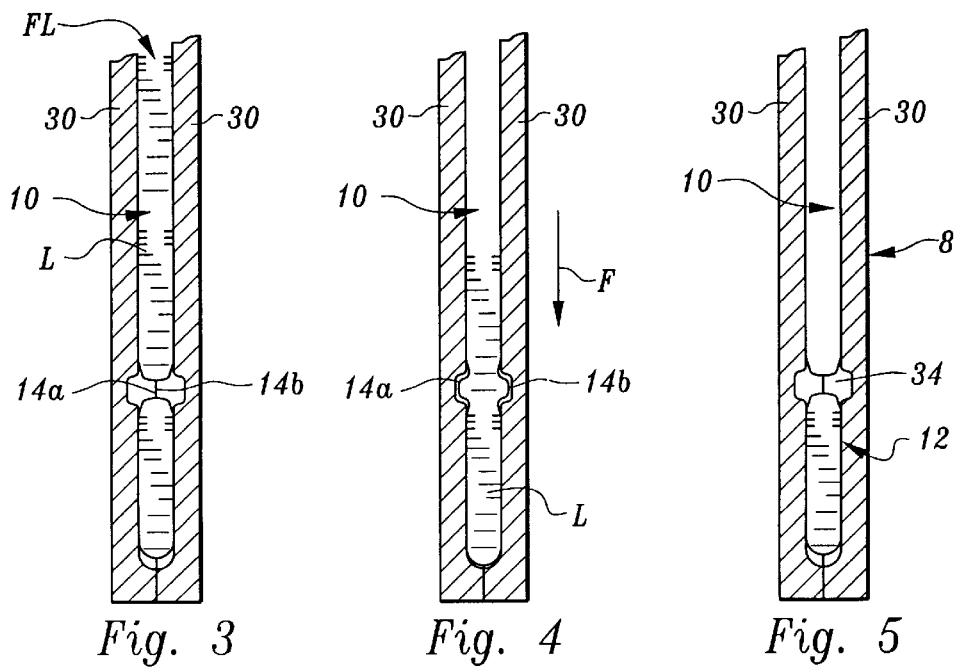

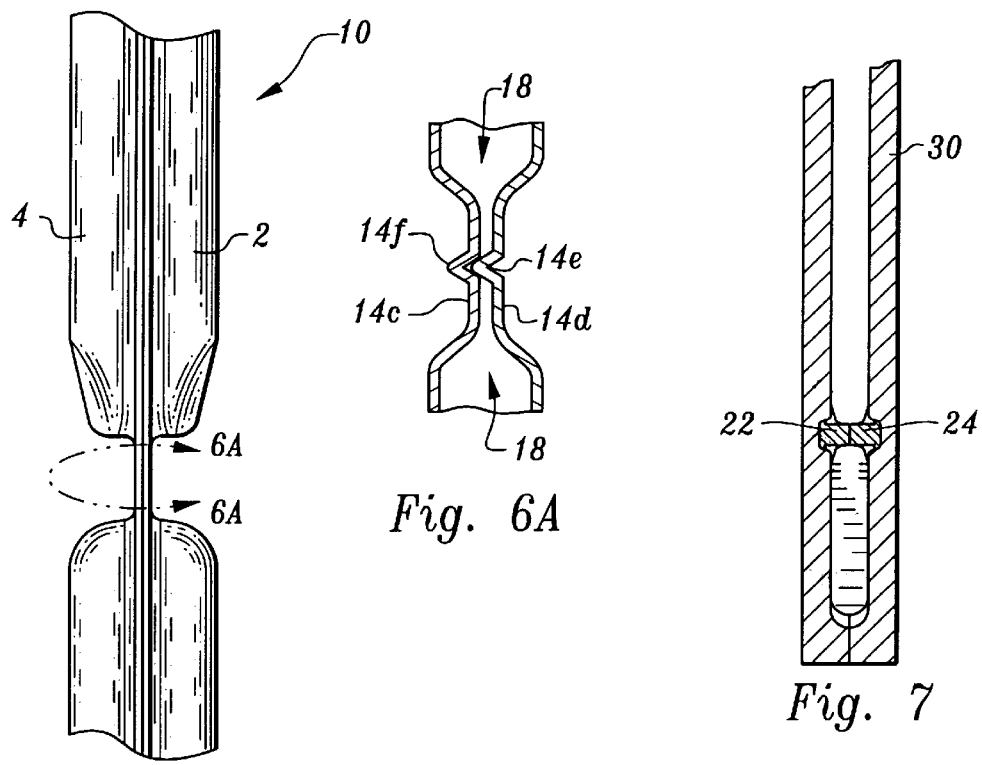
Fig. 6
Fig. 6A
Fig. 7
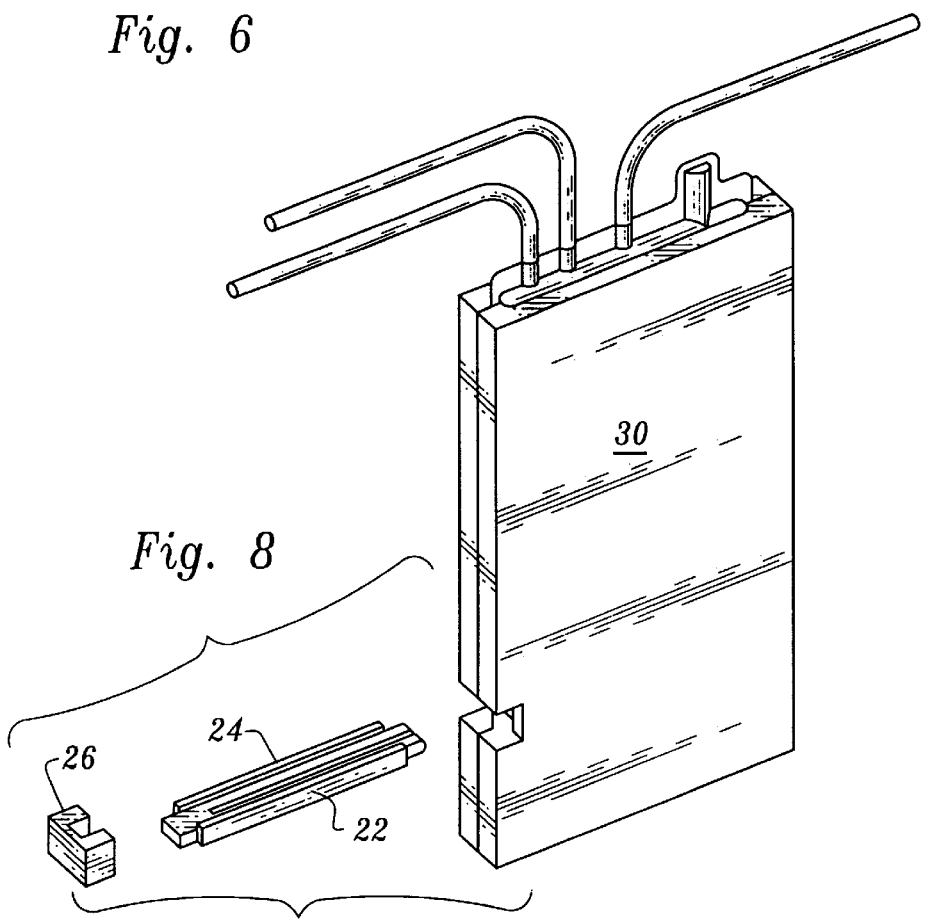
Fig. 8

CENTRIFUGATION BAG WITH YIELDABLE PARTITIONS

FIELD OF THE INVENTION

The following invention relates generally to an instrumentality which separates a fluid into two fractions based on sedimentation or precipitation and thereafter allows the fractions to be sequestered and one expressed from the other. More specifically, the instant invention is preferably directed to sequestering cryoprecipitate from plasma, or platelets from plasma, or any cellular components from plasma.

BACKGROUND OF THE INVENTION

Components in blood are routinely separated by centrifugation (i.e., red cells or white cells from plasma and platelets, platelets from plasma, cryoprecipitate from plasma, etc.

A variety of mechanical devices are utilized to attempt to sequester a specific one of these components into a specific volume without allowing the infiltration of any other components.

For instance, American Association of Blood Bank standards require substantially all of the platelets in a unit of blood should be collected into a total fluid volume of approximately 50 ml. Substantially all cryoprecipitated AHF from a unit of plasma should be collected in a volume not greater than 15 ml.

However, as all of these components are in fluid communication with each other, and all the mechanical devices in practice require the settling motion of the fluid common to all components in order to separate a specific component from the others, the subsequent currents generated by the fluid in motion necessarily starts recombining the components.

For example, consider separating platelet rich plasma which includes a minor fraction of red cells by subsequent centrifugation. One step requires expressing the platelet rich plasma into a processing bag whose initial weight is known and whose subsequent weight is determined after expressing the platelet rich plasma therein.

The plasma contained within the processing bag is centrifuged so that the platelets reside near the bottom of the processing bag upon a thin cushion of red cells leaving the lighter plasma stratified thereabove. The object is to sequester the overlying plasma away from the platelets, so that the platelets can be stored for subsequent therapeutic use. It has been determined that the platelets should be suspended in 50 ml. of plasma. Calculations heretofore have had to be performed in order to first tare out the plasma receiving bag and then continuously calculate (by weighing) as the plasma is put into the plasma bag in an amount sufficient to leave behind 50 ml. of suspended platelets within the platelet bag. This procedure is laborious from two vantage points.

From a first vantage point, the scale is influenced by the orientation of the connecting tube that communicates between the two bags. This can provide an unwanted torsion on the scale, skewing the reading. Second, transfer of the processing bag from a centrifuge station to an expressing station must be done with great care so as to not remix the stratified plasma overlying the platelets. Because the manual manipulation of this procedure requires great skill and clear calculation, efforts have been made to simplify these procedures.

The following prior art reflects the state of the art of which applicant is aware and is included herewith to discharge applicant's acknowledged duty to disclose relevant prior art. It is stipulated, however, that this reference does not teach singly nor render obvious when considered in any conceivable combination the nexus of the instant invention as disclosed in greater detail hereinafter and as particularly claimed.

OTHER PRIOR ART

One example of such a component separating device includes the NPBI Compomat® G4 automatic blood component blood processing system that attempts to automate blood component processing and provide uniform results. A bag is hung on a support proximate to an optical sensor adjacent a bag outlet and the bag is ensconced in a compartment. Pressure delivering instrumentalities within the machine push the fluid past the optical sensor through tubing into a bag on a scale to collect and weigh the expressed product. Computerized control responsive to the scale and optical sensor automates use of the process.

While this instrument abdicates to machinery many of the skill and computation steps required from the manual technique, the tubing still provides the opportunity for torsion on the balance, and the system can still not equal the results obtainable by extremely exact and careful manual manipulation. When a small volume of a blood component such as platelets are involved, maximum yield is necessary to assure efficacy for subsequent medical treatment during use of the platelets. In addition, the automated system is expensive and still especially prone to having the processing bag jostled during orientation on the machine.

SUMMARY OF THE INVENTION

The instant invention addresses the difficulties noted in the background of the invention by providing a new and novel processing bag which receives a blood component such as the platelet laden plasma, after its initial separation from a majority of the red cells, after a first centrifugation. The processing bag is formed from two "semirigid" shells, each shell being vacuum formed. The shells, after being joined face to face forming a hollow construct, display sufficient stiffness to maintain a substantially constant cross-section throughout the interior volume. The two shells, when joined together define a processing bag defining two volumes, one accessible to the other by means of a yieldable partition that allows selective migration between the two volumes in the presence of centrifugation force whereupon the yieldable partition moves from an at-rest, substantially closed position to an open position allowing the through passage of the fluid.

In a preferred embodiment, the first and second volumes are oriented in vertical registry for centrifugation separated one from the other by the yieldable partition. Upon centrifugation, the yieldable partition gives way to the force induced during centrifugation, opening the yieldable partition and allowing the deposition of predominantly all of the platelets upon a thin layer of the red cells in the lower (second) volume with the platelet poor plasma located thereabove in the upper (first) volume. During abatement of centrifugation, the yieldable partition has sufficient elasticity and memory to be restored to its original position in closed registry such that the first and second volumes are sequestered one from the other. Because the deceleration during centrifugation is gradual, the partition closes slowly, avoiding mixing and turbulence.

A yieldable clip may be employed after the sequestration into the first and second volumes to overlie the yieldable partition to reinforce the barrier that exists between the two volumes to afford easy decanting of the white cell poor plasma out of the first, upper volume.

Once the platelet poor plasma has been decanted, the yieldable clip can be removed to allow all of the contents within the second volume to reenter into the first volume. This first volume typically has a greater aggregate volume than the second volume. The larger first volume is a suitable environment for mixing a cryopreservative slowly and gently to the platelets prior to freezing storage in a freezer bag. Delivering a precisely repeatable fluid volume, containing substantially all the platelets in a unit of blood provides a product which can be packaged and stored more efficiently and frozen with a more repeatable rate of freezing.

OBJECTS OF THE INVENTION

Accordingly, it is a primary object of the present invention to provide a new and novel instrumentality which separates fluid and preferably any liquid (especially blood products) into different components.

A further object of the present invention is to provide a method associated with the apparatus for separating a fluid into two different components.

A further object of the present invention is to provide that which has been characterized above which is extremely economical to manufacture and lends itself to mass production techniques.

A further object of the present invention is to provide that which has been characterized above which is extremely accurate in use, allows itself to be manipulated by relatively unskilled technicians and affords precise, repeatable results.

A further object of the present invention as characterized above which provides both reliable sequestration of components of a product and easy decanting.

Viewed from a first vantage point, it is an object of the present invention to provide a separation bag, comprising, in combination: a first volume, a second volume, a yieldable means, between and normally closing the first and second volumes, to force externally generated upon a fluid contained within the bag to open in response to the force, whereupon the force on the yieldable means causes migration of a heavier fraction of the fluid from the first volume to the second volume and cessation of the force causes a gradual closing.

Viewed from a second vantage point, it is an object of the present invention to provide a method for separating components in a fluid, the steps including: placing the fluid into a bag, providing a yieldable partition to the bag which, when closed, defines first and second volumes in the bag, centrifuging the bag including the yieldable partition with a force sufficient to cause the yieldable partition to open, defining a single volume, allowing a heavier fraction of the fluid to migrate into the second volume during centrifugation, and stopping the centrifuging, causing the yieldable partition to close and resequester the first and second volumes.

Viewed from a third vantage point, it is an object of the present invention to provide two fluids having different densities derived from a single fluid, the process including: placing the single fluid in a bag, centrifuging the bag, opening the bag to its entire volume, and ceasing centrifuging, closing the bag into two volumes of differing densities.

These and other objects will be made manifest when considering the following detailed specification when taken in conjunction with the appended drawing figures.

BRIEF DESCRIPTION OF THE DRAWINGS

FIG. 1 is a front plan view of the processing bag according to the present invention with the yieldable clip removed.

FIG. 2 is a perspective view of the FIG. 1 bag and clip, with the clip deployed.

FIG. 3 is a sectional view of the bag within a construct showing the bag filled with fluid prior to centrifugation.

FIG. 4 is similar to FIG. 3 showing the bag during centrifugation.

FIG. 5 shows the bag similar to FIGS. 3 and 4 after centrifugation.

FIG. 6 is a detail of the bag showing a different variation on the yieldable partition shown in FIGS. 3 through 5.

FIG. 6A shows an alternative yieldable partition in exaggerated form.

FIG. 7 is a view similar to FIG. 3 showing yieldable clip prongs in place within a construct.

FIG. 8 is a perspective view of the construct and a two piece yieldable clip.

DESCRIPTION OF PREFERRED EMBODIMENTS

Referring to FIGS. 1 through 6, wherein like reference numerals refer to like parts throughout, reference numeral 10 is directed to the processing bag according to the present invention. Reference numeral 20 is directed to a resilient clip to be used in association therewith.

More particularly, and with reference to the drawing figures the processing bag 10 is formed from two shells 2, 4, one being essentially the mirror image of the other. Consequently, only one shell will be described.

Each shell (FIG. 1) includes a peripheral flange 6 which circumscribes the periphery of the central portion of the bag 10. The central portion of the bag is formed from two volumes. A first, upper volume 8 is separated from a second, lower volume 12 by means of a yieldable partition 14. Each shell is preferably formed via vacuum molding from a plastic material characterized in its ability to yield under heat and pressure when within the confines of a mold cavity whereupon, upon the release of the pressure and decrease of the elevated temperature associated therewith, the vacuum formed shell is fixed in position to retain its molded configuration.

The peripheral flange 6 of each shell is welded to its corresponding mate of the other shell such as by using RF technology, well known in the art. Other means for sealing the two shells together are contemplated as being within the metes and bounds of the instant invention, such as through solvents causing reaction along the face of the flanges, adhesives, or other type of molecular transfer between the two flanges providing a fluid resistant seal.

The yieldable partition 14, is not subjected to the sealing methodology noted above. Instead, each face 14a, 14b of the partition is placed in face to face registry with one another, but not sealed. Please see FIGS. 3 through 5. FIGS. 3 through 5 further reflect the bag 10 being placed within a construct 30. The construct 30 has an interior contour substantially complemental to the exterior dimension of the processing bag 10 and includes clearance 34 for expansion of the yieldable partition 14 as shown in FIG. 4. The construct 30 also benefits from the clearance 34 having a dimension complemental to the yieldable clip 20 shown in FIGS. 1 and 2. Thus, the clip 20 can be received on the bag 10 while still in the construct 30. FIG. 6A shows an alternative yieldable partition 14c and 14d in exaggerated form of that which is shown in FIG. 6. In this variation, the yieldable partition includes a projection 14e extending from one face of the yieldable partition 14 and a corresponding recess 14f which receives the projection 14e in tight, fluid sealing engagement. The remainder of the walls 14c and 14d are parallel throughout the remaining height of the partition 14 and communicate upstream and downstream from the yieldable partition in an outwardly converging nozzle 18 so that a gentle slope is found on the way through the yieldable partition thereby not providing a horizontal ledge which may provide an impediment for the through passage of material.

In use and operation, fluid FL is placed within the processing bag (FIG. 3) and placed within the construct 30. Subsequently, the bag 10 is exposed to centrifugation whereupon large dense particles L are caused to migrate below the yieldable partition. This occurs because the centrifugal force provides a downward force component F which acts upon the yieldable partition 14 forcing the partition open as shown in FIG. 4. Upon a requisite amount of centrifugation, the force F shown in FIG. 4 begins to abate and the elasticity of partition 14 causes it to slowly assume its unstressed state as shown in FIG. 5. This corresponds with the heavier fraction of the fluid FL being sequestered in the lower second volume 12 leaving the upper first volume 8 substantially devoid of these heavier elements which had been influenced by the centrifugation process and which opened the yieldable partition 14.

The clearance 34 allows the yieldable pin 20 shown in FIGS. 1 and 2 to be placed in overlying registry with respect to the partition 14. The yieldable clip is intended to make less likely that the separated fractions will be allowed to recoalesce during subsequent processing. As shown in FIGS. 1 and 2, a plurality of conduits C1, C2, C3 allow for the ingress and egress of fluids with respect to the bag 10. For example, conduit C1 may be used to introduce the whole fluid initially while conduit C2 may be used to decant the sequestered fluid from the upper volume 8. Conduit C3 may be used to introduce another fluid or removal of the contents from lower volume 12. As mentioned earlier, it is possible to overcome the resiliency of the yieldable partition 14 and allow the contents of the lower volume 12 to be reintroduced to the upper volume 8 after the upper volume 8 has been evacuated. By pressing along the direction of the arrows "P" of FIG. 1, the resilience of the partition 14 will give way and reopen the yieldable partition to allow removal of the contents of lower volume 12. The lower volume can be reintroduced into the upper volume 8 for subsequent processing.

The yieldable clip 20 includes resilient prongs defined by a first leg 22, the mirror image of a second leg 24, each made of resilient material having a tendency to remain in face to face tangential registry unless distended, for example by overlying the partition 14. The yieldable clip 20 includes a grasping area 26 to facilitate its manipulation. The grasping area 26 may be separable from the prongs 22, 24 and placed in an opening of the construct 30 to block access outside the construct during centrifugation (FIG. 8). The prongs 22, 24 may also be present during centrifugation, and their resiliency overcome by the centrifugal force F (FIG. 7). The yieldable clip 20 may also include a feathered leading edge 28 to facilitate its placement when overlying the partition 14.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A separation bag, comprising:
    a first shell and a second shell,
    said first shell being a mirror image of said second shell,
    each said shell being formed to include a peripheral flange and joined to form said bag,
    each said shell including a partition formed interiorly and integral with said shell such that said bag defines first and second volumes interrupted by tangential registry of said partitions from each said shell, said partitions are formed from a material of manufacture having a modulus of elasticity forcing said partitions out of tangential registry upon a requisite amount of centrifugation and closes when said centrifugation ceases,
    whereby large dense particles are caused to migrate beyond said partitions.

2. The bag of claim 1 wherein each said partition includes a preformed indentation on an outer surface of said bag to receive a yieldable clip thereover to further sequester said first volume from said second volume,
    said yieldable clip defined by first and second legs made of resilient material and biased to remain in face to face tangential registry.

3. The bag of claim 2 in combination with a construct having an interior contour complemental to an exterior dimension of said bag to overlie and ensconce said bag and said construct includes clearance for expansion of said partitions.

4. The bag of claim 3 wherein said construct includes an opening for receiving said yieldable clip therein, said opening in registry with said partitions.

5. The bag of claim 1 further including a recess disposed along a length of one of said partitions on said first shell dimensioned to receive a complementally formed projection disposed along a length of the other of said partitions on said second shell.

6. The bag of claim 5 wherein each said partition includes a performed indentation on an outer surface of said bag to receive a yieldable clip thereover to further sequester said first volume from said second volume,
    said yieldable clip defined by first and second legs made of resilient material and biased to remain in face to face tangential registry.

7. The bag of claim 1 wherein each said shell is characterized in its ability to yield under heat and pressure when confined in a mold cavity during shell formation and subsequently, after formation, each said shell retains its molded configuration.

8. The bag of claim 7 wherein said partitions include means to yield and open to centrifugal force and means to close when centrifugal force abates, and
    said partitions also open to pressure disposed along said peripheral flange aligned with a long axis of said partitions and means to close upon abatement of pressure.

9. The bag of claim 1 including a plurality of conduits formed in said bag and communicating with an interior of said bag.

10. The bag of claim 1 wherein upstream and downstream portions of said partitions define converging nozzles to provide a gentle slope.

11. A separation bag formed from first and second shells, said first shell a mirror image of said second shell, each said shell characterized in its ability to yield under heat and pressure when confined in a mold cavity during shell formation and subsequently, after formation, each said shell retains its molded configuration, each said shell formed to include a peripheral flange to join said first and second shells together, said bag when formed defining a substantially rectangular hollow box which retains its shape having a length, width and thickness, each said shell including a partition formed interiorly and integral with said shell such that said bag defines first and second volumes interrupted by tangential registry of said partitions from each said shell, said partitions are formed from a material of manufacture having a modulus of elasticity forcing said partitions out of tangential registry upon a requisite amount of centrifugation and closes when said centrifugation ceases, whereby large dense particles are caused to migrate beyond said partitions.

12. The bag of claim 11 in combination with a yieldable clip formed from first and second legs of resilient material, biased to stay closed, said clip dimensioned to overlie preformed indentations included on each of said partitions and disposed on an outer surface of said bag, to assist in forming said first and second volumes.

13. The bag of claim 12 further including a recess disposed along a length of one of said partitions on said first shell dimensioned to receive a complementally formed projection disposed along a length of the other of said partitions on said second shell.

14. The bag of claim 13 wherein upstream and downstream portions of said partitions define converging nozzles to provide a gentle slope.

15. The bag of claim 12 in combination with a construct having an interior contour complemental to an exterior dimension of said bag to overlie and ensconce said bag and said construct includes clearance for expansion of said partitions.

16. The bag of claim 15 wherein said construct includes an opening for receiving said yieldable clip therein, said opening in registry with said partitions.

17. The bag of claim 12 including a plurality of conduits formed in said bag and communicating with an interior of said bag.

18. A separation bag, comprising:

a first shell and a second shell;

said first shell being a mirror image of said second shell;

each said shell being formed to include a peripheral flange joined to form said bag;

each said shell including a partition formed interiorly and integral with said shell such that said bag defines first and second volumes interrupted by tangential registry of said partition from each said shell, said partitions are formed from a material of manufacture having a modulus of elasticity forcing said partitions out of tangential registry upon a requisite amount of centrifugation and closes when said centrifugation ceases wherein one partition includes a projection extending from its face and the other partition has a corresponding recess which receives the projection in tight fluid sealing engagement, whereby large dense particles are caused to migrate beyond said partition.

* * * * *